(12) United States Patent
Weiss et al.

(10) Patent No.: US 7,314,764 B2
(45) Date of Patent: *Jan. 1, 2008

(54) ORGANO LUMINESCENT SEMICONDUCTOR NANOCRYSTAL PROBES FOR BIOLOGICAL APPLICATIONS AND PROCESS FOR MAKING AND USING SUCH PROBES

(75) Inventors: Shimon Weiss, Pinole, CA (US); Marcel Bruchez, Jr., Albany, CA (US); Paul Alivisatos, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/370,656

(22) Filed: Mar. 7, 2006

(65) Prior Publication Data
US 2006/0177945 A1    Aug. 10, 2006

Related U.S. Application Data

(60) Division of application No. 10/918,622, filed on Aug. 12, 2004, now Pat. No. 7,101,718, which is a continuation of application No. 10/155,759, filed on May 24, 2002, now Pat. No. 6,927,069, which is a continuation of application No. 09/349,833, filed on Jul. 8, 1999, now Pat. No. 6,423,551, which is a continuation of application No. 08/978,450, filed on Nov. 25, 1997, now Pat. No. 5,990,479.

(51) Int. Cl.
*G01N 33/552* (2006.01)
(52) U.S. Cl. .................. 436/527; 435/6; 436/518; 436/524
(58) Field of Classification Search .............. None
See application file for complete search history.

(56) References Cited

U.S. PATENT DOCUMENTS 3,996,345 A   12/1976  Ullman et al. ............... 424/12

(Continued)

FOREIGN PATENT DOCUMENTS

EP        0 990 903        4/2000

(Continued)

OTHER PUBLICATIONS

Alivisatos, A. P., "Semiconductor Clusters, Nanocrystals, and Quantum Dots," *Science* 271 (Feb. 16, 1996):933-937.

(Continued)

*Primary Examiner*—Christopher L. Chin
(74) *Attorney, Agent, or Firm*—Karl Bozicevic; Bozicevic, Field & Francis LLP

(57) ABSTRACT

A semiconductor nanocrystal compound is described capable of linking to an affinity molecule. The compound comprises (1) a semiconductor nanocrystal capable of emitting electromagnetic radiation and/or absorbing energy, and/or scattering or diffracting electromagnetic radiation—when excited by an electromagnetic radiation source or a particle beam; and (2) an affinity molecule linked to the semiconductor nanocrystal. The semiconductor nanocrystal is linked to an affinity molecule to form a semiconductor nanocrystal probe capable of bonding with a detectable substance. Exposure of the semiconductor nanocrystal to excitation energy will excite the semiconductor nanocrystal causing the emission of electromagnetic radiation. Further described are processes for respectively: making the luminescent semiconductor nanocrystal compound; making the semiconductor nanocrystal probe; and using the probe to determine the presence of a detectable substance in a material.

14 Claims, 3 Drawing Sheets

U.S. PATENT DOCUMENTS

| | | | | |
|---|---|---|---|---|
| 4,637,988 | A | 1/1987 | Hinshaw et al. | 436/546 |
| 4,777,128 | A | 10/1988 | Lippa | 435/5 |
| 5,262,357 | A | 11/1993 | Alivisatos et al. | 437/233 |
| 5,319,209 | A | 6/1994 | Miyakawa et al. | 250/459.1 |
| 5,505,928 | A | 4/1996 | Alivisatos et al. | 423/299 |
| 5,537,000 | A | 7/1996 | Alivisatos et al. | 313/506 |
| 5,585,640 | A | 12/1996 | Huston et al. | 250/483.1 |
| 5,674,698 | A | 10/1997 | Zarling et al. | 435/7.92 |
| 5,736,330 | A | 4/1998 | Fulton | 435/6 |
| 5,751,018 | A | 5/1998 | Alivisatos et al. | 257/64 |
| 5,990,479 | A * | 11/1999 | Weiss et al. | 250/307 |
| 6,023,540 | A | 2/2000 | Walt et al. | |
| 6,423,551 | B1 * | 7/2002 | Weiss et al. | 436/518 |
| 6,927,069 | B2 * | 8/2005 | Weiss et al. | 436/518 |
| 7,101,718 | B2 * | 9/2006 | Weiss et al. | 436/524 |

FOREIGN PATENT DOCUMENTS

| | | |
|---|---|---|
| EP | 1 271 154 A2 | 1/2003 |
| WO | WO 98/04740 | 2/1998 |
| WO | WO 99/19515 | 4/1999 |

OTHER PUBLICATIONS

Alivisatos, A. P., "Perspectives on the Physical Chemistry of Semiconductor Nanocrystals," *J. Phys. Chem.* 100 (1996):13226-13239.

Alivisatos, A. Paul, et al., "Organization of 'Nanocrystal Molecules' Using DNA," *Nature* 382 (Aug. 15, 1996):609-611.

Beverloo, H.B., et al., "Preparation and Microscopic Visualization of Multicolor Luminescent Immunophosphors," Chapter 4 of Beverloo, H. B., "Inorganic Crystals as Luminescent Labels: Their Applications in Immunocytochemistry and Time-Resolved Microscopy," Ph.D. dissertation, University of Leiden (The Netherlands), May 13, 1992, pp. 553-573.

Bruchez, Marcel P., Jr., "Luminescent Semiconductor Nanocrystals: Intermittent Behavior and Use as Fluorescent Biological Probes," Ph.D. dissertation, University of California, Dec. 17, 1998.

Bruchez, Marcel, Jr., et al., "Semiconductor Nanocrystals as Fluorescent Probes for Biology", *Cytometry Supp.* 9 (1998):26.

Chan, Warren C.W., et al., "Quantum Dot Bioconjugates for Ultrasensitive Nonisotopic Detection," *Science* 281 (Sep. 25, 1998):2016-2018.

Coffer, Jeffrey L., et al., "Characterization of Quantum-Confined CdS Nanocrystallites Stablized by Deoxyribonucleic Acid (DNA)," *Nanotechnol.* 3 (1992):69-76.

Cook, Neil D., "Scintillation Proximity Assay: A Versatile High-Throughput Screening Technology," *Drug Discovery Today* 1 (Jul. 1996):287-294.

Correa-Duarte, Miguel A., et al., "Stabilization of CdS Semiconductor Nanoparticles Against Photodegradation by a Silica Coating Procedure," *Chem. Phys. Lett.* 286 (Apr. 17, 1998):497-501.

Jacoby, Mitch, "Quantum Dots Meet Biomolecules," *C&E News* 76 (Sep. 28, 1998):Copied from the Internet as pp. 1-3.

Kagan, C. R., et al, "Electronic Energy Transfer in CdSe Quantum Dot Solids," *Phys. Rev. Lett.* 76 (Feb. 26, 1996):1517-1520.

Leff, David N., "Color-Coding Quantum Dots Debut with Promising Careers in Clinical Diagnostics Field," *Bioworld Today*, Sep. 25, 1998, Copied from the Internet as pp. 1-2.

Liz-Marzán, Luis M., et al., "Synthesis of Nanosized Gold-Silica Core-Shell Particles," *Langmuir* 12 (1996):4329-4335.

Mahtab, Rahina, et al., "Preferential Adsorption of a 'Kinked' DNA to a Neutral Curved Surface: Comparisons to and Implications for Nonspecific DNA-Protein Interactions," *J. Am. Chem. Soc.* 118 (1996):7028-7032.

Mahtab, Rahina, et al., "Protein-Sized Quantum Dot Luminescence Can Distinguish Between 'Straight,' 'Bent,' and 'Kinked' Oligonucleotides," *J. Am. Chem. Soc.* 117 (1995):9099-9100.

Murphy, Catherine J., et al. , "Quantum Dots as Inorganic DNA-Binding Proteins," *Mat. Res. Soc. Symp. Proc.* 452 (1997):597-600.

Peng, Xiaogang, et al., "Synthesis and Isolation of a Homodimer of Cadmium Selenide Nanocrystals," *Angewandte Chemie-International Edition in English*, 36 (1997):145-147.

Service, Robert F., "Semiconductor Beacons Light Up Cell Structures," *Science* 281 (Sep. 25, 1998):1930-1931.

Shröck, E., et al., "Multicolor Spectral Karyotyping of Human Chromosomes," *Science* 273 (Jul. 26, 1996):494-497.

Zhang, Yu-zhong, et al., "Novel Flow Cytometry Compensation Standards: Internally Strained Fluorescent Microspheres with Matched Emission Spectra and Long-Term Stability," *Cytometry* 33 (1998):244-248.

Lacoste, T.D., et al., "Super Resolution Molecular Ruler Using Single Quantum Dots", *Biophysical Journal*, vol. 78, Jan. 2000, p. 402A, XP-000933548 Abstract.

Bruchez, Marcel, Jr., et al., "Semiconductor Nanocrystals as Fluorescent Biological Labels", *Science*, vol. 281, Sep. 25, 1998, pp. 2013-2016.

Dabbousi, B.O., et al., "(CdSe) ZnS Core-Shell Quantum Dots: Synthesis and Characterization of a Size Series of Highly Luminescent Nanocrystal-lites", *Journal of Physical Chemistry B*, vol. 101, 1997, pp. 9463-9475.

Peng, Xiaogang, et al., "Epitaxial Growth of Highly Luminescent CdSe/CdS Core/Shell Nanocrystals with Photostability and Electronic Accessibility", *Journal of the American Chemical Society*, vol. 119, No. 30, pp. 7019-7029.

* cited by examiner

LINKING TOGETHER A SEMICONDUCTOR NANOCRYSTAL CAPABLE OF EMITTING RADIATION IN A NARROW WAVELENGTH BAND
AND
ONE OR MORE LINKING AGENTS CAPABLE OF ALSO LINKING TO AN ORGANIC AFFINITY MOLECULE;

AND
LINKING TOGETHER AN ORGANIC AFFINITY MOLECULE CAPABLE OF SELECTIVELY BONDING WITH A DETECTABLE SUBSTANCE
AND
THE ONE OR MORE LINKING AGENTS CAPABLE OF ALSO LINKING TO A SEMICONDUCTOR NANOCRYSTAL;

TO THEREBY FORM AN ORGANO LUMINESCENT SEMICONDUCTOR NANOCRYSTAL PROBE CAPABLE OF BONDING TO A DETECTABLE SUBSTANCE IN A MATERIAL AND, FOR EXAMPLE, TO EMIT RADIATION OF A NARROW WAVELENGTH BAND WHEN EXPOSED TO EXCITATION ENERGY TO INDICATE THE PRESENCE OF THE DETECTABLE SUBSTANCE

FIG. 4

DETERMINING THE PRESENCE OF A DETECTABLE SUBSTANCE IN A BIOLOGICAL MATERIAL BY CONTACTING THE BIOLOGICAL MATERIAL WITH AN ORGANO LUMINESCENT SEMICONDUCTOR NANOCRYSTAL PROBE COMPRISING:

1. A SEMICONDUCTOR NANOCRYSTAL CAPABLE OF EMITTING, ABSORBING, SCATTERING, OR DIFFRACTING ENERGY IN A NARROW FREQUENCY BAND WHEN EXCITED;

2. AN AFFINITY MOLECULE CAPABLE OF BONDING TO THE DETECTABLE SUBSTANCE; AND

3. ONE OR MORE LINKING AGENTS CAPABLE OF LINKING TO BOTH THE SEMICONDUCTOR NANOCRYSTAL AND THE AFFINITY MOLECULE

---

REMOVING FROM THE BIOLOGICAL MATERIAL PORTIONS OF THE ORGANO LUMINESCENT SEMICONDUCTOR NANOCRYSTAL PROBE NOT BONDED TO THE DETECTABLE SUBSTANCE

---

EXPOSING THE BIOLOGICAL MATERIAL TO ENERGY CAPABLE OF EXCITING THE SEMICONDUCTOR NANOCRYSTAL IN ANY ORGANO-LUMINESCENT DETECTION COMPOUND PRESENT IN THE BIOLOGICAL MATERIAL TO EMIT, ABSORB, SCATTER OR DIFFRACT ENERGY

---

DETECTING ANY ENERGY EMITTED AND/OR ANY ABSORBED, AND/OR SCATTERED OR DIFFRACTED BY THE SEMICONDUCTOR NANOCRYSTAL INDICATING THE PRESENCE IN THE BIOLOGICAL MATERIAL OF ANY DETECTABLE SUBSTANCE BONDED TO THE ORGANO-LUMINESCENT DETECTION COMPOUND

FIG. 5

ORGANO LUMINESCENT SEMICONDUCTOR NANOCRYSTAL PROBES FOR BIOLOGICAL APPLICATIONS AND PROCESS FOR MAKING AND USING SUCH PROBES

CROSS-REFERENCE TO RELATED APPLICATION

This application is a divisional of U.S. patent application Ser. No. 10/918,622 filed Aug. 12, 2004 now U.S. Pat. No. 7,101,718 which is a continuation of U.S. patent application Ser. No. 10/155,759 filed May 24, 2002, now U.S. Pat. No. 6,927,069 issued Aug. 9, 2005 which application is a continuation of U.S. patent application Ser. No. 09/349,833 filed Jul. 8, 1999, now U.S. Pat. No. 6,423,551 issued Jul. 23, 2002 which application is a continuation of U.S. patent application Ser. No. 08/978,450 filed Nov. 25, 1997, now U.S. Pat. No. 5,990,479 issued Nov. 23, 1999 all of which are incorporated herein by reference in their entirety and to which applications we claim priority under 35 USC §120.

The invention described herein arose in the course of, or under, Contract No. DE-AC03-SF00098 between the United States Department of Energy and the University of California for the operation of the Ernest Orlando Lawrence Berkeley National Laboratory. The Government may have rights to the invention.

BACKGROUND OF THE INVENTION

1. Field of the Invention

This invention relates to organo luminescent semiconductor nanocrystal probes for biological applications wherein the probes includes a plurality of semiconductor nanocrystals capable of luminescence and/or absorption and/or scattering or diffraction when excited by a radiation or particle beam.

2. Description of the Related Art

Fluorescent labeling of biological systems is a well known analytical tool used in modern biotechnology as well as analytical chemistry. Applications for such fluorescent labeling include technologies such as medical (and non-medical) fluorescence microscopy, histology, flow cytometry, fluorescence in-situ hybridization (medical assays and research), DNA sequencing, immuno-assays, binding assays, separation, etc.

Conventionally, such fluorescent labeling involves the use of an organic dye molecule bonded to a moiety which, in turn, selectively bonds to a particular biological system, the presence of which is then identified by excitation of the dye molecule to cause it to fluoresce. There are a number of problems with such an analytical system. In the first place, the emission of light of visible wavelengths from an excited dye molecule usually is characterized by the presence of a broad emission spectrum as well as a broad tail of emissions on the red side of the spectrum, i.e., the entire emission spectrum is rather broad. As a result, there is a severe limitation on the number of different color organic dye molecules which may be utilized simultaneously or sequentially in an analysis since it is difficult to either simultaneously or even non-simultaneously detect or discriminate between the presence of a number of different detectable substances due to the broad spectrum emissions and emission tails of the labelling molecules. Another problem is that most dye molecules have a relatively narrow absorption spectrum, thus requiring either multiple excitation beams used either in tandem or sequentially for multiple wavelength probes, or else a broad spectrum excitation source which is sequentially used with different filters for sequential excitation of a series of probes respectively excited at different wavelengths.

Another problem frequently encountered with existing dye molecule labels is that of photostability. Available fluorescent molecules bleach, or irreversibly cease to emit light, under repeated excitation ($10^4$-$10^8$) cycles of absorption/emission. These problems are often surmounted by minimizing the amount of time that the sample is exposed to light, and by removing oxygen and/or other radical species from the sample.

In addition, the probe tools used for the study of these systems by electron microscopy techniques are completely different from the probes used for study by fluorescence. Thus, it is not possible to label a material with a single type of probe for both electron microscopy and for fluorescence.

It would, therefore, be desirable to provide a stable probe material for biological applications having a wide absorption band and capable of exhibiting either a detectable change in absorption or of emitting radiation in a narrow wavelength band, without the presence of the large red emission tails characteristic of dye molecules (thereby permitting the simultaneous use of a number of such probe materials, each emitting light of a different narrow wavelength band) and/or capable of scattering or diffracting radiation. It would also be equally desirable to provide a single, stable probe material which can be used to image the same sample by both light and electron microscopy.

SUMMARY OF THE INVENTION

The invention comprises a luminescent semiconductor nanocrystal compound capable of linking to an affinity molecule to form an organo luminescent semiconductor nanocrystal probe capable of luminescence and/or absorption and/or scattering or diffracting when excited by an electromagnetic radiation source (of broad or narrow bandwidth) or a particle beam, and capable of exhibiting a detectable change in absorption and/or of emitting radiation in a narrow wavelength band and/or scattering or diffracting when so excited. The luminescent semiconductor nanocrystal compound preferably comprises: (1) a semiconductor nanocrystal capable of luminescence and/or absorption and/or scattering or diffraction when excited by an electromagnetic radiation source (of broad or narrow bandwidth) or a particle beam, and capable of exhibiting a detectable change in absorption and/or of emitting radiation in a narrow wavelength band and/or scattering or diffracting when excited; and (2) a linking agent having a first portion linked to the semiconductor nanocrystal, and a second portion capable of linking to an affinity molecule.

The invention further comprises an organo luminescent semiconductor nanocrystal probe formed by linking the above described luminescent semiconductor nanocrystal compound to an affinity molecule capable of bonding to a detectable substance in a material. As a result the organo luminescent semiconductor nanocrystal probe, in one embodiment, is capable of absorbing or scattering or diffracting energy from either a particle beam or an electromagnetic radiation source (of broad or narrow bandwidth), and is capable of emitting electromagnetic radiation in a narrow wavelength band when so excited; while in another embodiment the amount of energy so absorbed, or scattered, or diffracted from either a particle beam or an electromagnetic radiation source (of broad or narrow bandwidth), is detectable, i.e., the change in absorption, scattering, or diffraction is detectable.

Therefore, treatment of a material with the organo luminescent semiconductor nanocrystal probe, and subsequent exposure of this treated material to excitation energy (from either a particle beam or an electromagnetic radiation source of broad or narrow bandwidth) to determine the presence of the detectable substance within the material, will excite the semiconductor nanocrystals in the organo luminescent semiconductor nanocrystal probe bonded to the detectable substance, resulting in the emission of electromagnetic radiation of a narrow wavelength band and/or a detectable change in the amount of energy being absorbed and/or scattered or diffracted, signifying the presence, in the material, of the detectable substance bonded to the organo luminescent semiconductor nanocrystal probe.

The invention also comprises a process for making the luminescent semiconductor nanocrystal compound and for making the organo luminescent semiconductor nanocrystal probe comprising the luminescent semiconductor nanocrystal compound linked to an affinity molecule capable of bonding to a detectable substance. The organo luminescent semiconductor nanocrystal probe of the invention is stable with respect to repeated excitation by light, or exposure to oxygen or other radicals. The invention further comprises a process for treating a material, such as a biological material, to determine the presence of a detectable substance in the material which comprises contacting the material with the organo luminescent semiconductor nanocrystal probe, removing from the material portions of the organo luminescent semiconductor nanocrystal probe not bonded to the detectable substance, and then exposing the material to activation energy from either an electromagnetic radiation source (of broad or narrow bandwidth) or a particle beam. The presence of the detectable substance in the material is then determined either by measuring the absorption of energy by the organo luminescent semiconductor nanocrystal probe and/or detecting the emission of radiation of a narrow wavelength band by the organo luminescent semiconductor nanocrystal probe and/or detecting the scattering or diffraction by the organo luminescent semiconductor nanocrystal probe, indicative (in either case) of the presence of the organo luminescent semiconductor nanocrystal probe bonded to the detectable substance in the material.

BRIEF DESCRIPTION OF THE DRAWINGS

FIG. 4 is a flow sheet illustrating the process of forming the organo luminescent semiconductor nanocrystal probe of the invention.

FIG. 5 is a flow sheet illustrating a typical use of the organo luminescent semiconductor nanocrystal probe of the invention in detecting the presence of a detectable substance in a material such as a biological material.

DETAILED DESCRIPTION OF THE INVENTION

Figure 1:
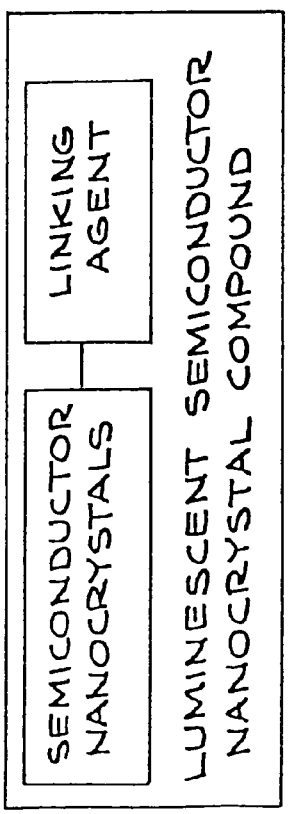
FIG. 1 is a block diagram of the luminescent semiconductor nanocrystal compound of the invention.
Figure 2:
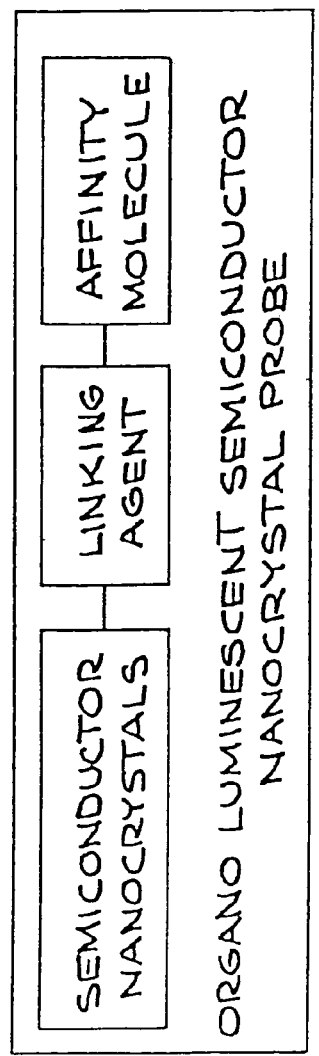
FIG. 2 is a block-diagram of the organo luminescent semiconductor nanocrystal probe of the invention.
Figure 3:
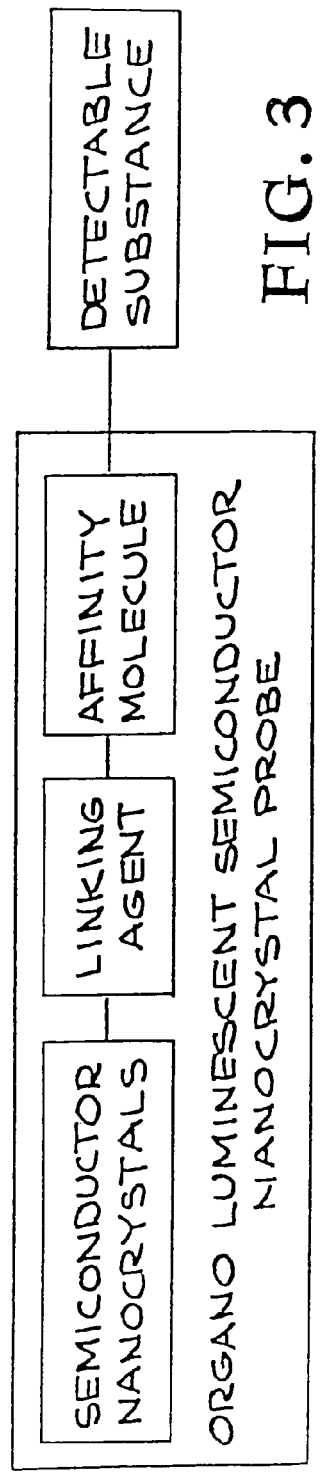
FIG. 3 is a block diagram showing the affinity between a detectable substance and the organo luminescent semiconductor nanocrystal probe of the invention.

The invention comprises a luminescent semiconductor nanocrystal compound capable of linking to an organic molecule and capable of exhibiting a detectable change in absorption and/or of emitting electromagnetic radiation in a narrow wavelength band and/or scattering or diffracting when excited by either an electromagnetic radiation source (of broad or narrow bandwidth) or a particle beam. The luminescent semiconductor nanocrystal compound, in turn, comprises: (1) semiconductor nanocrystals capable of exhibiting a detectable change in absorption and/or of emitting electromagnetic radiation in a narrow wavelength band when excited by either an electromagnetic radiation source (of broad or narrow bandwidth) or a particle beam; and (2) one or more linking agents each having a first portion linked to the semiconductor nanocrystal and a second portion capable of linking to an organic affinity molecule.

The invention also comprises the above described luminescent semiconductor nanocrystal compound linked to the organic affinity molecule (through the linking agent) to form an organo luminescent semiconductor nanocrystal probe capable of bonding to a detectable substance and capable of exhibiting a detectable change in absorption and/or of emitting electromagnetic radiation in a narrow wavelength band and/or scattering or diffracting when excited by either an electromagnetic radiation source (of broad or narrow bandwidth) or a particle beam. Treatment of a material (typically a biological material) with the organo luminescent semiconductor nanocrystal probe, and subsequent exposure of this treated material to excitation energy, as described above, to determine the presence of the detectable substance within the material, will excite the semiconductor nanocrystal in the organo luminescent semiconductor nanocrystal probe bonded to the detectable substance, causing the detectable change in absorption and/or emission of electromagnetic radiation of a narrow wavelength band and/or scattering or diffraction signifying (in either instance) the presence in the material, of the detectable substance bonded to the organo luminescent semiconductor nanocrystal probe.

The invention also comprises a process for making the luminescent semiconductor nanocrystal compound, and a process for making the organo luminescent semiconductor nanocrystal probe comprising the luminescent semiconductor nanocrystal compound linked to an affinity molecule capable of bonding to a detectable substance.

The invention further comprises a process for treating a material, such as a biological material, to determine the presence of a detectable substance in the material which comprises: (1) contacting the material with the organo luminescent semiconductor nanocrystal probe, (2) removing from the material portions of the organo luminescent semiconductor nanocrystal probe not bonded to the detectable substance, (3) exposing the material to energy (such as the above-described electromagnetic energy source or particle beam) capable of exciting the semiconductor nanocrystal to cause a detectable change in absorption and/or emission of electromagnetic radiation of a narrow wavelength band and/or scattering or diffraction signifying (in either instance) the presence of the organo luminescent semiconductor nanocrystal probe bonded to the detectable substance in the material, and (4) detecting either the change in absorbed energy or the electromagnetic radiation emitted or the scattering or diffraction by the semiconductor nanocrystal in the organo luminescent semiconductor nanocrystal probe.

a. Definitions

By use of the terms "nanometer crystal" or "nanocrystal" herein is meant an organic or inorganic single crystal particle having an average cross-section no larger than about 20 nanometers (nm) or $20 \times 100^{-9}$ meters (200 Angstroms), preferably no larger than about 10 nm (100 Angstroms) and a minimum average cross-section of about 1 nm, although in some instances a smaller average cross-section nanocrystal, i.e., down to about 0.5 nm (5 Angstroms), may be acceptable. Typically the nanocrystal will have an average cross-section ranging in size from about 1 nm (10 Angstroms) to about 10 nm (100 angstroms).

By use of the term "semiconductor nanocrystal" is meant a nanometer crystal or nanocrystal of Group II-VI and Group III-V semiconductor compounds capable of emitting electromagnetic radiation upon excitation, although the use of Group IV semiconductors such as germanium or silicon, or the use of organic semiconductors, may be feasible under certain conditions.

By use of the term "a narrow wavelength band", with regard to the electromagnetic radiation emission of the semiconductor nanocrystal, is meant a wavelength band of emissions not exceeding about 40 nm, and preferably not exceeding about 20 nm in width and symmetric about the center, in contrast to the emission bandwidth of about 100 nm for a typical dye molecule, with a red tail which may extend the band width out as much as another 100 nm. It should be noted that the bandwidths referred to are determined from measurement of the width of the emissions at half peak height (FWHM), and are appropriate in the range of 200 nm to 2000 nm.

By use of the term "a broad absorption band", with regard to the electromagnetic radiation absorption of the semiconductor nanocrystal is meant a continuously increasing absorption from the onset, which occurs near to, but at slightly higher energy than the "narrow wavelength band" of the emission. This is in contrast to the "narrow absorption band" of dye molecules which occurs near the emission peak on the high energy side, but drops off rapidly away from that wavelength.

By use of the term "detectable substance" is meant an entity or group, the presence or absence of which in a material such as a biological material, is to be ascertained by use of the organo-luminescent semiconductor nanocrystal probe of the invention.

By use of the term "affinity molecule" is meant the portion of the organo luminescent semiconductor nanocrystal probe of the invention which will selectively bond to a detectable substance (if present) in the material (e.g., biological material) being analyzed.

By use of the term "linking agent" is meant a substance capable of linking with a semiconductor nanocrystal and also capable of linking to an affinity molecule.

The terms "link" and "linking" are meant to describe the adherence between the affinity molecule and the semiconductor nanocrystals, either directly or through a moiety identified herein as a linking agent. The adherence may comprise any sort of bond, including, but not limited to, covalent, ionic, hydrogen bonding, Van der Waals' forces, or mechanical bonding, etc.

The terms "bond" and "bonding" are meant to describe the adherence between the affinity molecule and the detectable substance. The adherence may comprise any sort of bond, including, but not limited to, covalent, ionic, or hydrogen bonding, Van der Waals' forces, or mechanical bonding, etc.

The term "luminescent semiconductor nanocrystal compound", as used herein, is intended to define a semiconductor nanocrystal linked to one or more linking agents and capable of linking to an affinity molecule, while the term "organo-luminescent semiconductor nanocrystal probe" is intended to define a luminescent semiconductor nanocrystal compound linked to an affinity molecule.

The term "glass" as used herein is intended to include one or more oxides of silicon, boron, and/or phosphorus, or a mixture thereof, as well as the further optional inclusion of one or more metal silicates, metal borates or metal phosphates therein.

b. The Semiconductor Nanocrystals

The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe; and nanocrystals of Group III-V semiconductors such as GaAs, InGaAs, InP, and InAs. As mentioned above, the use of Group IV semiconductors such as germanium or silicon, or the use of organic semiconductors, may also be feasible under certain conditions.

Formation of nanometer crystals of Group III-V semiconductors is described in copending and commonly assigned Alivisatos et al. U.S. Pat. No. 5,751,018; Alivisatos et al. U.S. Pat. No. 5,505,928; and Alivisatos et al. U.S. Pat. No. 5,262,357, which also describes the formation of Group II-VI semiconductor nanocrystals, and which is also assigned to the assignee of this invention. Also described therein is the control of the size of the semiconductor nanocrystals during formation using crystal growth terminators. The teachings of Alivisatos et al. U.S. Pat. No. 5,751,018, and Alivisatos et al. U.S. Pat. No. 5,262,357 are each hereby specifically incorporated by reference.

In a preferred embodiment, the nanocrystals are used in a core/shell configuration wherein a first semiconductor nanocrystal forms a core ranging in diameter, for example, from about 20 Å to about 100 Å, with a shell of another semiconductor nanocrystal material grown over the core nanocrystal to a thickness of, for example, 1-10 monolayers in thickness. When, for example, a 1-10 monolayer thick shell of CdS is epitaxially grown over a core of CdSe, there is a dramatic increase in the room temperature photoluminescence quantum yield. Formation of such core/shell nanocrystals is described more fully in a publication by one of us with others entitled "Epitaxial Growth of Highly Luminescent CdSe/CdS Core/Shell Nanocrystals with Photostability and Electronic Accessibility", by Peng, Schlamp, Kadavanich, and Alivisatos, published in the Journal of the American Chemical Society, Volume 119, No. 30. 1997, at pages 7019-7029, the subject matter of which is hereby specifically incorporated herein by reference.

The semiconductor nanocrystals used in the invention will have a capability of emitting light within a narrow wavelength band of about 40 nm or less, preferably about 20 nm or less, thus permitting the simultaneous use of a plurality of differently colored organo luminescent semiconductor nanocrystal probes with different semiconductor nanocrystals without overlap (or with a small amount of overlap) in wavelengths of emitted light (unlike the use of dye molecules with broad emission lines (e.g., ~100 nm) and broad tails of emission (e.g., another 100 nm) on the red side of the spectrum), thus allowing for the simultaneous detection of a plurality of detectable substances.

c. Affinity Molecule

The particular affinity molecule forming a part of the organo-luminescent semiconductor nanocrystal probe of the invention will be selected based on its affinity for the particular detectable substance whose presence or absence, for example, in a biological material, is to be ascertained. Basically, the affinity molecule may comprise any molecule capable of being linked to a luminescent semiconductor nanocrystal compound which is also capable of specific recognition of a particular detectable substance. In general, any affinity molecule useful in the prior art in combination with a dye molecule to provide specific recognition of a detectable substance will find utility in the formation of the organo-luminescent semiconductor nanocrystal probes of the invention. Such affinity molecules include, by way of example only, such classes of substances as monoclonal and polyclonal antibodies, nucleic acids (both monomeric and oligomeric), proteins, polysaccharides, and small molecules such as sugars, peptides, drugs, and ligands. Lists of such affinity molecules are available in the published literature such as, by way of example, the "Handbook of Fluorescent Probes and ResearchChemicals", (sixth edition) by R. P. Haugland, available from Molecular Probes, Inc.

d. The Linking Agent

The organo-luminescent semiconductor nanocrystal probe of the invention will usually find utility with respect to the detection of one or more detectable substances in organic materials, and in particular to the detection of one or more detectable substances in biological materials. This requires the presence, in the organo-luminescent semiconductor nanocrystal probe, of an affinity molecule or moiety, as described above, which will bond the organo-luminescent semiconductor nanocrystal probe to the detectable substance in the organic/biological material so that the presence of the detectable material may be subsequently ascertained. However, since the semiconductor nanocrystals are inorganic, they may not bond directly to the organic affinity molecule. In these case therefore, there must be some type of linking agent present in the organo-luminescent semiconductor nanocrystal probe which is capable of forming a link to the inorganic semiconductor nanocrystal as well as to the organic affinity molecule in the organo-luminescent semiconductor nanocrystal probe.

One form in which the semiconductor nanocrystal may be linked to an affinity molecule via a linking agent is by coating the semiconductor nanocrystal with a thin layer of glass, such as silica ($SiO_x$ where x=1-2), using a linking agent such as a substituted silane, e.g., 3-mercaptopropyl-trimethoxy silane to link the nanocrystal to the glass. The glass-coated semiconductor nanocrystal may then be further treated with a linking agent, e.g., an amine such as 3-aminopropyl-trimethoxysilane, which will function to link the glass-coated semiconductor nanocrystal to the affinity molecule. That is, the glass-coated semiconductor nanocrystal may then be linked to the affinity molecule. It is within the contemplation of this invention that the original luminescent semiconductor nanocrystal compound may also be chemically modified after it has been made in order to link effectively to the affinity molecule. A variety of references summarize the standard classes of chemistry which may be used to this end, in particular the "Handbook of Fluorescent Probes and Research Chemicals", (6th edition) by R. P. Haugland, available from Molecular Probes, Inc., and the book "Bioconjugate Techniques", by Greg Hermanson, available from Academic Press, New York.

When the semiconductor nanocrystal is coated with a thin layer of glass, the glass, by way of example, may comprise a silica glass ($SiO_x$ where x=1-2), having a thickness ranging from about 0.5 nm to about 10 nm, and preferably from about 0.5 nm to about 2 nm.

The semiconductor nanocrystal is coated with the coating of thin glass, such as silica, by first coating the nanocrystals with a surfactant such as tris-octyl-phosphine oxide, and then dissolving the surfactant-coated nanocrystals in a basic methanol solution of a linking agent, such as 3-mercapto-propyl-tri-methoxy silane, followed by partial hydrolysis which is followed by addition of a glass-affinity molecule linking agent such as amino-propyl trimethoxysilane which will link to the glass and serve to form a link with the affinity molecule.

When the linking agent does not involve the use of a glass coating on the semiconductor nanocrystal, it may comprise a number of different materials, depending upon the particular affinity molecule, which, in turn, depends upon the type of detectable material being analyzed for. It should also be noted that while an individual linking agent may be used to link to an individual semiconductor nanocrystal, it is also within the contemplation of the invention that more than one linking agent may bond to the same semiconductor nanocrystal and vice versa.

A few examples of the types of linking agents which may be used to link to both the semiconductor nanocrystal (or to a glass coating on the nanocrystal) and to the organic affinity molecule in the probe are illustrated in the table below, it being understood that this is not intended to be an exhaustive list:

| Linking Agent | |
|---|---|
| Structure | Name |
|  | N-(3-aminopropyl)3-mercapto-benzamide |
| 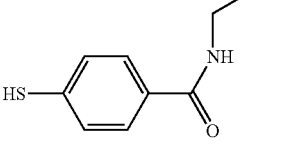 | 3-aminopropyl-trimethoxysilane |
| 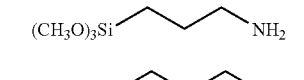 | 3-mercaptopropyl-trimethoxysilane |
| 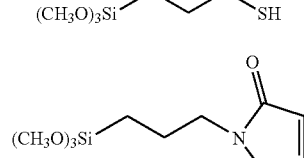 | 3-maleimidopropyl-trimethoxysilane |
| 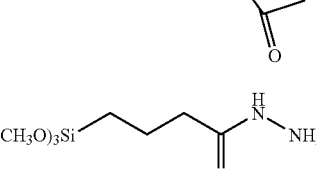 | 3-hydrazidopropyl-trimethoxysilane |

It should be further noted that a plurality of polymerizable linking agents may be used together to form an encapsulating net or linkage around an individual nanocrystal (or group of nanocrystals). This is of particular interest where the particular linking agent is incapable of forming a strong bond with the nanocrystal. Examples of linking agents capable of bonding together in such a manner to surround the nanocrystal with a network of linking agents include, but are not limited to: diacetylenes, acrylates, acrylamides, vinyl, styryl, and the aforementioned silicon oxide, boron oxide, phosphorus oxide, silicates, borates and phosphates.

e. The Excitation of the Probe and Detection of Emission/Absorption

As previously mentioned, the organo luminescent semiconductor nanocrystal probe of the invention is capable of being excited over a broad bandwidth, yet exhibits emission in a narrow wavelength band, in contrast to the dye molecules used in the prior art. Thus electromagnetic radiation of wavelength ranging from x-ray to ultraviolet to visible to infrared waves may be used to excite the luminescent semiconductor nanocrystals in the probe. In addition, the luminescent semiconductor nanocrystals are capable of excitation from bombardment with a particle beam such as an electron beam (e-beam). Furthermore, because of the broad bandwidth at which the luminescent semiconductor nanocrystals are excitable, one may use a common excitation source for the simultaneous excitation of several probes, i.e., several probes which give off radiation at different frequencies, thus permitting simultaneous excitation and detection of the presence of several probes indicating, for example, the presence of several detectable substances in the material being examined.

Thus, for example, a laser radiation source of a given frequency, e.g., blue light, may be used to excite a first organo luminescent semiconductor nanocrystal probe capable of emitting radiation of a second frequency, e.g., red light, indicating the presence, in the material being illuminated, of a first detectable substance to which the particular red light-emitting organo luminescent semiconductor nanocrystal probe has bonded. At the same time, the same blue light laser source may also be exciting a second organo luminescent semiconductor nanocrystal probe (in the same material) capable of emitting radiation of a third frequency, e.g., green light, indicating the presence, in the material being illuminated, of a second detectable substance to which the particular green light-emitting organo luminescent semiconductor nanocrystal probe has bonded. Thus, unlike the prior art, multiple excitation sources need not be used (because of the broad bandwidth in which the organo luminescent semiconductor nanocrystal probe of the invention is capable of being excited), and the narrow band of emission of the specific semiconductor nanocrystals in each probe makes possible the elimination of sequencing and/or elaborate filtering to detect the emitted radiation.

With respect to the absorption of energy by the probe of the invention, when the excitation source is an electron beam, or an X-ray source, the presence of the organo luminescent semiconductor nanocrystal probe bonded to the detectable substance of interest in the material being analyzed can be ascertained using a commercially available energy absorption or scattering or diffraction detection system wherein changes in absorption or scattering cross section or in diffraction of the material being analyzed can be detected, signifying the presence of the probe in the material, which, in turn, indicates the presence of the detectable substance to which the probe is bonded in the material being analyzed. In addition, it may be possible to use electron or X-ray sources to detect the presence of the organo luminescent semiconductor nanocrystal probe bonded to the detectable substance by using a conventional detection system for the emission of visible light to observe the visible emission in the narrow wavelength of emission of the probe.

The following examples will serve to further illustrate the formation of the organo luminescent semiconductor nanocrystal probes of the invention, as well as their use in detecting the presence of a detectable substance in a material such as a biological material.

EXAMPLE 1

To illustrate the formation of the luminescent semiconductor nanocrystal compound (comprising the semiconductor nanocrystals linked to a linking agent) 20 ml. of a 5 mM solution of (4-mercapto)benzoic acid was prepared with a pH of 10 using $(CH_3)_4NOH \cdot 5H_2O$. 20 mg of tris-octylphosphine oxide coated CdSe/CdS core/shell nanocrystals were added to the solution and stirred until completely dissolved. The resultant nanocrystal/linking agent solution was heated for 5 hours at 50-60° C. and then concentrated to a few ml by evaporation. Then an equal volume of acetone was added and the nanocrystals precipitate out of solution homogeneously. The precipitate was then washed with acetone, dried, and then can be stored.

The luminescent semiconductor nanocrystal compound prepared above can be linked with an appropriate affinity molecule to form the organo luminescent semiconductor nanocrystal probe of the invention to treat a biological material to determine the presence or absence of a detectable substance. That is, the luminescent semiconductor nanocrystal compound prepared above can be linked, for example, with avidin or streptavidin (as the affinity molecule) to form an organo luminescent semiconductor nanocrystal probe to treat a biological material to ascertain the presence of biotin; or the luminescent semiconductor nanocrystal compound prepared above can be linked with anti-digoxiginen to form an organo luminescent semiconductor nanocrystal probe to treat a biological material to ascertain the presence of digoxiginen.

EXAMPLE 2

To illustrate the formation of luminescent semiconductor nanocrystal compound (comprising glass-coated semiconductor nanocrystals linked to a linking agent), 50 μl of 3-mercaptopropyl-trimethoxy silane was added to 40 ml of an anhydrous solution of 25 vol. % dimethylsulfoxide in methanol, and the pH was adjusted to 10-11 using $(CH_3)_4NOH \cdot 5H_2O$. 10 mg of tris-octylphosphine oxide coated CdSe/CdS core-shell particles, prepared by the technique described in the aforementioned Peng, Schlamp, Kadavanich, and Alivisatos article, were then dissolved in this solution, and stirred for several hours. The solution was diluted with 40 ml of methanol adjusted to a pH of 10 with $(CH_3)_4NOH \cdot 5H_2O$, and heated for 1 hour at 69° C. The solution was stirred for an hour, and 40 ml of a 90 vol. % methanol/9.89 vol. % $H_2O$/0.1 vol. % trimethoxysilylpropyl urea/0.01 vol. % aminopropyl-trimethoxy silane solution which had been stirring for at least an hour, was added, and stirred for 2 hours. Subsequently the reaction was heated to 69° C. for 15 minutes, and then cooled. 10 ml of a 10 vol. % chlorotrimethyl silane solution in methanol which had been adjusted to a pH of 10 using $(CH_3)_4NOH \cdot 5H_2O$ was added, stirred for 2 hours, then heated to 60° C., and then partially concentrated under vacuum. Once the methanol had all evaporated, the solution was precipitated with acetone as an oil product comprising the luminescent semiconductor nanocrystal compound. The luminescent semiconductor nanocrystal compound may then be redissolved in water, and in a variety of buffer solutions to prepare it for linking it to an affinity molecule to form the organo luminescent semiconductor nanocrystal probe of the invention to treat a biological material to determine the presence or absence of a detectable substance.

Thus, the invention provides an organo luminescent semiconductor nanocrystal probe containing a semiconductor nanocrystal capable, upon excitation by either electromagnetic radiation (of either narrow or broad bandwidth) or particle beam, of emitting electromagnetic radiation in a narrow wavelength band and/or absorbing energy and/or scattering or diffracting said excitation, thus permitting the simultaneous usage of a number of such probes emitting different wavelengths of electromagnetic radiation to thereby permit simultaneous detection of the presence of a number of detectable substances in a given material. The probe material is stable in the presence of light or oxygen, capable of being excited by energy over a wide spectrum, and has a narrow band of emission, resulting in an improved material and process for the simultaneous and/or sequential detection of a number of detectable substances in a material such as a biological material.

What is claimed is:

1. An organo-luminescent semiconductor nanocrystal probe structure, comprising:
    (a) a semiconductor nanocrystal which emits light when excited; and
    an affinity molecule linked to the semiconductor nanocrystal.

2. The probe of claim 1, wherein the affinity molecule is linked to the semiconductor nanocrystal by a linking group.

3. The probe of claim 1, wherein the affinity molecule is a biological material.

4. The probe of claim 1, wherein the affinity molecule is an antibody.

5. The probe of claim 4, wherein the antibody is a monoclonal antibody.

6. The probe of claim 1, wherein the affinity molecule is a nucleic acid.

7. The probe of claim 6, wherein the nucleic acid is monomeric.

8. The probe of claim 6, wherein the nucleic acid is oligomeric.

9. The probe of claim 1, wherein the affinity molecule is a protein.

10. The probe of claim 1, wherein the affinity molecule is a polysaccharide.

11. The probe of claim 1, wherein the affinity molecule is a sugar.

12. The probe of claim 1, wherein the affinity molecule is a peptide.

13. The probe of claim 1, wherein the affinity molecule is a drug.

14. The probe of claim 1, further comprising:
    a detectable substance bound to the affinity molecule.

* * * * *